United States Patent
Lee et al.

(10) Patent No.: US 8,545,903 B2
(45) Date of Patent: Oct. 1, 2013

(54) COMPOSITION FOR THE PREVENTION AND TREATMENT OF INFLUENZA VIRUS INFECTION AND COMPOSITION FOR SUPPRESSING NEURAMINIDASE ACTIVITY COMPRISING TURMERIC EXTRACT

(75) Inventors: Woo-Song Lee, Jeonllabukdo (KR); Mun-Chual Rho, Jeonllabukdo (KR); Su-Jin Park, Gwangju (KR); Young-Bae Ryu, Gyeongsangnam-do (KR); Jong-Sun Chang, Jeonllabukdo (KR); Mal-Sun Shin, Jeonllabukdo (KR); Hyung-Jae Jeong, Gyeongsangnam-do (KR); Hyung-Jun Kwon, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/383,132

(22) PCT Filed: Jul. 8, 2010

(86) PCT No.: PCT/KR2010/004455
§ 371 (c)(1),
(2), (4) Date: Jan. 9, 2012

(87) PCT Pub. No.: WO2011/005043
PCT Pub. Date: Jan. 13, 2011

(65) Prior Publication Data
US 2012/0107429 A1    May 3, 2012

(30) Foreign Application Priority Data

Jul. 8, 2009  (KR) .................. 10-2009-0062321
Sep. 9, 2009  (KR) .................. 10-2009-0085112

(51) Int. Cl.
*A01N 65/00*    (2009.01)

(52) U.S. Cl.
USPC ........................................... 424/725

(58) Field of Classification Search
None
See application file for complete search history.

(56) References Cited

FOREIGN PATENT DOCUMENTS

| CN | 1674875 A1 | 9/2005 |
| JP | 2008-280333 | 11/2008 |
| KR | 10-2007-0102487 | 10/2007 |

OTHER PUBLICATIONS

J. Agnc.Food Chem. (2002) 50(13) pp. 3668-3672.

*Primary Examiner* — Michael Meller
(74) *Attorney, Agent, or Firm* — Meunier Carlin & Curfman, LLC

(57) ABSTRACT

Disclosed is a composition comprising a turmeric extract for preventing and treating influenza virus infection and for inhibiting neuraminidase activity. A turmeric extract, its fraction, and a curcuminoid-based compound separated therefrom may inhibit neuraminidase activity and have antiviral and cell degeneration inhibitory effects on influenza virus, and may be useful in preventing and treating influenza virus infection.

9 Claims, No Drawings

COMPOSITION FOR THE PREVENTION AND TREATMENT OF INFLUENZA VIRUS INFECTION AND COMPOSITION FOR SUPPRESSING NEURAMINIDASE ACTIVITY COMPRISING TURMERIC EXTRACT

CROSS REFERENCE TO RELATED APPLICATIONS

This application is a 35 USC 371 national phase of International Application No. PCT/KR2010/004455 filed Jul. 8, 2010, which claims priority to KR Patent Application No. 10-2009-0062321 filed Jul. 8, 2009, and KR Patent Application No. 10-2009-0085112 filed Sep. 9, 2009, the contents of all of which are hereby incorporated herein by reference in their entirety.

BACKGROUND

1. Field

The present invention relates to a composition comprising a turmeric extract for the prevention and treatment of influenza virus infection and the inhibition of neuraminidase activity.

2. Description of Related Art

Influenza virus is one of the most infective viruses that cause acute respiratory diseases, and in severe instances, cause herd infection or pandemic over the world, particularly giving rise to serious respiratory symptoms in children, the aged, patients with cardiopulmonary diseases, and the like (Hien, T. T. et al. *N. Eng. J. Med.,* 350, 1179, 2004). Influenza virus is a genus of the Orthomyxovirus and has three types, that is, A, B, and C. Among them, particularly A and B types routinely spread in people. Influenza virus has eight RNA gene segments, and two glycoproteins, hemagglutinin (HA) and neuraminidase (NA) that are a type of surface antigen found on the surface of the influenza virus. Hemagglutinin is a trimer with a head and a stalk, and the head of the trimer involves a majority of antigenic variation. Hemagglutinin binds to terminal sialic acid residues on the surface of host cells to enable viruses to attach to and enter in the host cells in sequence (Chandrasekaran, A. et al. *Nature biotechnology* 26, 107, 2008). Neuraminidase is a mushroom-shaped tetramer with a head and a stalk, and the head of the tetramer has active sites on the top surfaces thereof. Neuraminidase cleaves the alpha-ketosidic bond between oligosacchrides at cell surfaces and terminal neuraminic acid residues to assist viruses replicated and proliferated in the infected cells to exit outside the host cells and enter in the respiratory mucosa cells (a. Mark, V. I. *Nature review* 6, 967, 2007. b. Huberman, K. et al. *Virology* 214, 294, 1995).

The same subtype of virus surface antigen produces an antigenic variation to generate new antigenic variants every year. Particularly, among influenza viruses, avian influenza virus, which is still a threat undergoes an antigenic shift to infect various kinds of birds such as chickens, turkeys, ducks, wild birds, and the like. Avian influenza virus spreads so quickly that once a chicken is infected, 80% or more of the chickens are killed. Avian influenza virus which poses the most damage and threat to the poultry industry over the world causes viral diseases, and this pervasive effect is not just limited to the poultry industry. It has been reported that avian influenza virus can infect humans, which causes diseases to spread among humans (Gubareva, L. V. et al. *Lancet.* 355, 2000). In past ages, influenza virus has been known to cause many diseases. Specifically, there have been three flu pandemics in the twentieth century, Spanish flu pandemic (H1N1) which killed about thirty millions, the Asian Flu (H2N2) which killed and an estimated one million and the Hong Kong Flu (H3N2) which also killed an estimated one million. Later, in 2003 to 2008, 385 were infected and 243 died. Recently, the World Health Organization (WHO) officially announced that the novel swine-origin influenza break out of April, 2009 as being pandemic. As of Jun. 29, 2009, 70,893 people (including 311 deaths) in over 115 countries were infected, and a South Korean nun visiting Mexico for volunteer work has been confirmed as the first flu patient on May 2, 2009. As of Aug. 16, 2009, a cumulative number of 2,089 flu patients (including 2 deaths) were reported in South Korea.

To prevent and treat the influenza virus infection, consideration may be made to inhibit the absorption in epithelial cells, the invasion into cells, the transcription or replication of genes, the synthesis of proteins, or the release from cells, each having been the focus of the antiviral studies.

To treat diseases caused by influenza virus, four substances, that is, Amatadine, Rimatadine, Zanamivir, and Oseltamivir have been used with the approval of Food and Drug Administration (FDA). As older M2 inhibitors, Amatadine and Rimatadine have antiviral effects by blocking an ion channel of a membrane protein, particularly M2 protein that is essential to the proliferation of virus to inhibit the uncoating of the virus, but are only effective against influenza A virus. Also, it is reported that the virus becomes more tolerant and resistant to the substances as a consequence of being used over 40 years, and severe side effects occur in the nervous system and stomach (Bantia, S. et al. *Antiviral Research* 69, 39, 2006). Since 1999, as new drugs to treat virus infection, Zanamivir and Oseltamivir called neuraminidase inhibitors have been used, which play an important role in proliferation of virus, have a low prevalence of tolerance, and are active against both influenza A and B viruses (Zhang, J. et al. *Bioorg. Med. Chem. Lett.* 16, 3009, 2006).

However, Zanamivir has an advantage of high antiviral effects but is disadvantageous in low bioavailability and quick release from the kidney, and Oseltamivir causes severe vomiting (Ryan, D. M. et al. *Antimicrob. Agents Chemother.,* 39, 2583, 1995).

As mentioned above, existing antivirals have serious side effects and require considerable caution in their application. Also, the development effects of vaccines are low when the vaccine virus is not matched to circulating viruses. Accordingly, there is an increasing need for a new influenza antiviral with excellent infection inhibition and stability.

To satisfy the need, the inventors invented the present invention after discovering that a turmeric extract, its fraction or a curcuminoid-based compound separated therefrom has neuraminidase inhibitory activity, and antiviral and cell degeneration inhibitory effects.

DISCLOSURE

It is an object of the present invention to provide a pharmaceutical composition for preventing and treating influenza virus infection and a treatment method using the same.

It is another object of the present invention to provide a food composition for preventing and reducing influenza virus infection.

It is yet another object of the present invention to provide a quasi-drug composition for preventing and reducing influenza virus infection.

It is still another object of the present invention to provide a neuraminidase inhibitor composition for inhibiting the activity of neuraminidase present in various biospecies to treat diseases caused thereby, and an inhibition method using the same.

EFFECT OF THE INVENTION

The composition comprising the turmeric extract, fraction, and curcuminoid-based compound separated therefrom according to the present invention may inhibit neuraminidase activity and have antiviral and cell degeneration inhibitory effects, and thus may be useful in preventing and treating influenza virus infection.

BEST MODE

To achieve this object, in an aspect of the present invention, a composition comprising a turmeric extract or its fraction as an active ingredient to prevent and treat influenza virus infection is provided.

In another aspect of the present invention, a composition comprising a compound represented by the following chemical formula 1 as an active ingredient to prevent and treat influenza virus infection is provided:

[Chemical formula 1]

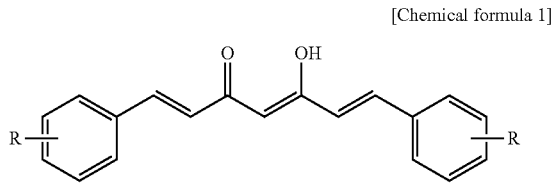

where R is independently hydrogen, a hydroxyl group, or $C_1$-$C_{10}$ alkoxy group.

In another aspect of the present invention, a use of a turmeric extract, a turmeric fraction, or a compound represented by the following chemical formula 1 in preventing and treating influenza virus infection, or a use of a turmeric extract, a turmeric fraction, or a compound represented by the following chemical formula 1 in preparing a drug for preventing and treating influenza virus infection is provided.

In another aspect of the present invention, a method for treating influenza virus infection is provided, including administering, to an individual infected or to be infected with influenza virus, a composition comprising a turmeric extract, a turmeric fraction, or a compound represented by the following chemical formula 1 as an active ingredient to prevent and treat influenza virus infection:

[Chemical formula 1]

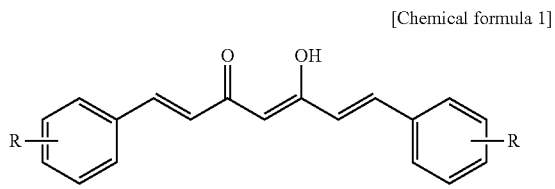

where R is independently hydrogen, a hydroxyl group, or $C_1$-$C_{10}$ alkoxy group.

In another aspect of the present invention, a composition comprising a turmeric extract, a turmeric fraction, or a compound represented by the following chemical formula 1 as an active ingredient to inhibit neuraminidase activity is provided:

[Chemical formula 1]

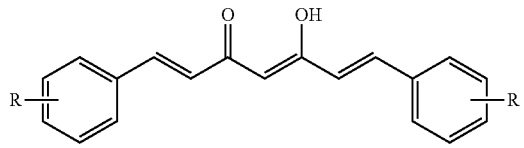

where R is independently hydrogen, a hydroxyl group, or $C_1$-$C_{10}$ alkoxy group.

In another aspect of the present invention, a method for inhibiting neuraminidase activity including contacting the composition with a sample containing neuraminidase is provided.

Hereinafter, the present invention is described in more detail.

The present invention provides a composition comprising a turmeric extract or its fraction as an active ingredient to prevent and treat influenza virus infection.

The composition of the present invention may inhibit the activity of neuraminidase that is found on the surface of the influenza virus and plays an essential role in replicating the virus, and may prevent the influenza virus from spreading to other cells in the respiratory organ, thereby reducing, preventing, and treating influenza virus infection.

The term "prevent" described herein refers to all activities to inhibit the influenza virus infection or retard the pathogenesis of the influenza virus infection by administering the composition.

The term "treat" described herein refers to all activities to improve or favorably change the symptoms of the influenza virus infection by administering the composition.

The influenza virus refers to a strain of influenza virus that may cause diseases to human or animal individuals, and may be influenza A virus, influenza B virus, or influenza C virus which are identified by differences in nucleoprotein and matrix protein. The influenza A virus, influenza B virus, and influenza C virus may include their variants. The influenza virus subtypes are mainly classified on the basis of characteristics of hemaglutinin (HA) and neuraminidase (NA), and to date, 6 types of HAs (H1-H6) and 9 types of NAs (N-1-N9) have been reported. Preferably, the influenza virus may be H1N1 influenza virus or H9N2 influenza virus, more preferably rvH1N1 influenza A virus, H1N1 influenza virus (A/PR/8/34), or H9N2 influenza virus (A/Chicken/Korea/MS96/96). The influenza virus may cause influenza, cold, laryngopharyngitis, bronchitis, pneumonia, and particularly, bird flu, swine flu, or goat flu.

Generally, a turmeric is a tuberous root of *Curcuma longa* Linne as it is or a tuberous root of *Curcuma longa* Linne steamed and dried after removing the periderm (the Korean Pharmacopoeia $9^{th}$ Edition), and the "tuberous root" called a storage root is a thickened root.

In the present invention, a turmeric refers to a tuberous root of a plant of *Curcuma* sp. including, but not limited to, *Curcuma wenyujin* (Y. H. Chen et C. Ling), *Curcuma longa* Linne, *Curcuma longa* Salisb., *Curcuma zedoaria, Curcuma kwansiensis* (S. G. Lee et C. F. Liang), *Curcuma aeruginosa, Curcuma phaeocaulis* Val. (Zingiberaceae), and *Curcuma domestica*.

For example, *Curcuma longa* Linne has a rhizome by *Curcuma longa Rhizoma* (the Korean Pharmacopoeia $9^{th}$ Edition), and the "rhizome" called a rootstalk refers to a stem of a plant creeping underground like a root.

Plants of *Curcuma* sp. have a "tuberous root" and a "rhizome".

Among plants of *Curcuma* sp., the measurement results of the content of a curcumin derivative in an ethanol extract of *Curcuma longa* Linne for area showed that 17.0 g/kg of curcumin, 5.3 g/kg of demethoxycurcumin, and 3.4 g/kg of bisdemethoxycurcumin were detected in a tuberous root, these compounds were not detected in a stem, and 2.8 g/kg of curcumin, 0.4 g/kg of demethoxycurcumin, and 6.8 g/kg of bisdemethoxycurcumin were detected in a rhizome (Example 4).

In the present invention, a turmeric extract may be obtained from different organs of native plants, hybrids, or varieties, preferably a tuberous root or a plant tissue culture.

In the present invention, a turmeric may be available on the market, may be collected in nature, or may be obtained from cultivated products.

In another aspect of the present invention, a method for preparing a composition having activity against neuraminidase is provided, including extracting a turmeric with a solvent of water, $C_1$-$C_4$ alcohol, or mixtures thereof to obtain a turmeric extract.

Also, the method may further comprise fractioning the turmeric extract with hexane, ethylacetate, or water.

Also, the method may include separating and purifying the turmeric fraction.

The obtaining of the turmeric extract may use conventional extraction techniques in the art, including, but not limited to, for example ultrasonic extraction, maceration, heat extraction, cold extraction, filtration, reflux extraction, and the like. The extraction may be performed at room temperature or by heating under such conditions as to eliminate or minimize the destruction of an active ingredient. Also, the extraction may use a variety of solvents known in the art, including, but not limited to, for example water, $C_1$-$C_4$ alcohol, acetone, ethylacetate, chloroform, or mixtures thereof. Preferably, the turmeric extract may be obtained by washing a turmeric root to remove an impurity, drying, milling, and extracting with a solvent of water, $C_1$-$C_4$ alcohol, or mixtures thereof, more preferably $C_1$-$C_4$ alcohol, most preferably methanol or ethanol. In this instance, the content of the extractant, that is, the solvent used may be preferably twice to twenty times as much the dried weight of the turmeric. For example, the alcohol extract may be obtained by drying the turmeric, cutting fine, putting in an extract container, adding a solvent of lower $C_1$-$C_4$ alcohol or mixtures thereof, preferably methanol or ethanol, placing at room temperature for a predetermined time, and filtering. In this instance, the predetermined time is preferably a week, and concentration or freeze-drying may be further performed.

The extract of the present invention may include at least one of an extract obtained by extraction, a diluent or a concentrate of an extract, a dried extract obtained by drying an extract, and a product obtained by crudely purifying or purifying an extract.

The turmeric fraction of the present invention may be obtained by fractioning the turmeric extract. To obtain the turmeric fraction, a variety of solvents known in the art may be used. For example, the solvents may include pentane, hexane, 2,2,4-trimethylpentane, dicainum, cyclohexane, carbon disulfide, carbon tetrachloride, chlorobutane, diisopropylether, chloroform, acetone, nitropropane, butanone, dichloroethane, pyridine, propanol, methanol, ethylacetate, and butanol. More specifically, the turmeric fraction may be obtained by suspending the turmeric extract in water, and sequentially fractioning with hexane and ethylacetate to yield a hexane fraction, an ethylacetate fraction, and a water fraction.

Also, the present invention provides a composition comprising a compound represented by the following chemical formula 1 as an active ingredient to prevent and treat influenza virus infection:

[Chemical formula 1]

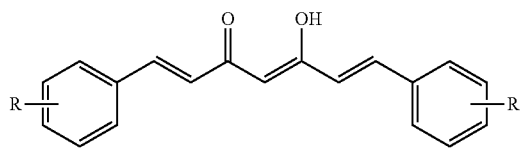

where R is independently hydrogen, a hydroxyl group, or $C_1$-$C_{10}$ alkoxy group.

In this instance, the compound represented by chemical formula 1 may be separated from the turmeric extract or turmeric fraction. More specifically, the compound represented by chemical formula 1 may be a compound represented by any one of the following chemical formulas 2 to 4.

[Chemical formula 2]

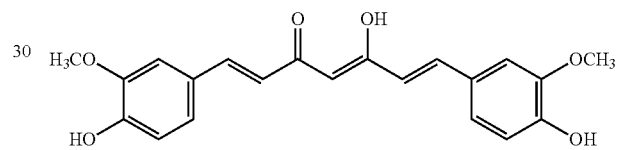

[Chemical formula 3]

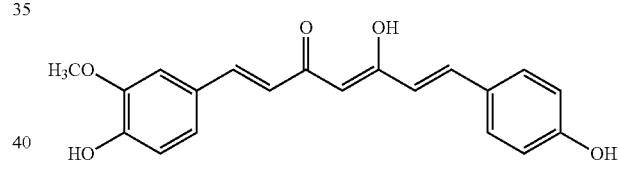

[Chemical formula 4]

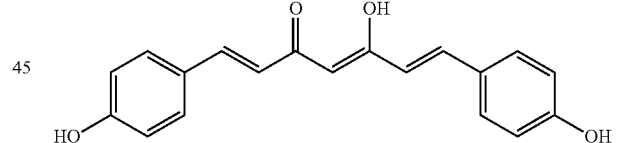

Also, the present invention provides a method for separating the compound represented by chemical formula 1 from a turmeric, including a) extracting the turmeric with a solvent of water, $C_1$-$C_4$ alcohol, or mixtures thereof to yield a turmeric extract, b) obtaining a hexane fraction, an ethylacetate fraction, or a water fraction from the extract, and c) separating and purifying the fraction.

More specifically, the compound represented by chemical formula 1 according to the present invention may be a representative active ingredient present in a turmeric, and a method for separating the compound may be performed below.

First, a turmeric may be extracted with a solvent of water, $C_1$-$C_4$ alcohol, or mixtures thereof to obtain a turmeric extract (step 1). The turmeric is not particularly limited, and may be available on the market or from cultivated products. The turmeric may be used after washing and drying. The alcohol may be lower alcohol such as methanol, ethanol, propanol, or butanol, preferably methanol or ethanol.

In step 1, the turmeric extract may be obtained by drying a turmeric under the shade, cutting fine, milling to improve the extraction efficiency, putting in an extract container, adding a proper amount of alcohol, placing at room temperature for 5 days, and filtering through a filter paper and the like. This process may be repeated several times, and thereafter concentration or freeze-drying may be further performed.

Subsequently, the turmeric extract obtained in step 1 may be suspended in water and sequentially fractioned with hexane and ethylacetate to obtain a turmeric fraction (step 2). In this instance, typical fractional extraction may be used, preferably using a separatory funnel. The turmeric fraction may be a hexane fraction, an ethylacetate fraction, or a water fraction.

Next, the turmeric fraction obtained in step 2 may be separated by silica gel chromatography, followed by purification, to obtain the compound represented by chemical formula 1 (step 3). When silica gel chromatography is used for separation, solvents of n-hexane, n-hexane/ethylacetate, chloroform/acetone, and methanol may be preferably used as mobile phases. Also, a mixed solvent of n-hexane/acetone may be additionally used. In this instance, a ratio by volume of n-hexane and ethylacetate may be preferably 50:1 to 1:5, and a ratio by volume of chloroform and acetone may be preferably 150:1 to 1:4. The chromatography may be performed 1 to several times until a single compound is obtained, and when needed, concentration or re-crystallization may be performed.

Also, the compound represented by chemical formula 1 according to the present invention may be used in the form of a pharmaceutically acceptable salt, preferably an acid addition salt formed by a pharmaceutically acceptable free acid. The acid addition salt may be obtained from inorganic acids such as hydrochloric acid, nitric acid, phosphoric acid, sulfuric acid, hydrobromic acid, hydroiodic acid, nitrous acid, phosphorous acid, and the like, or non-toxic organic acids such as aliphatic monocarboxylate, aliphatic dicarboxylate, phenyl-substituted alkanoate, hydroxyalkanoate, hydroxyalkandioate, aromatic acids, aliphatic and aromatic sulfonic acids, and the like. The pharmaceutically non-toxic salt may include sulfate, pyrosulfate, bisulfate, sulfite, bisulfate, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methybenzoate, dinitrobenzoate, hydroxybenzoate, methoxybenzoate, phthalate, terephthalte, benzene sulfonate, toluene sulfonate, chloro benzene sulfonate, xylene sulfonate, phenyl acetate, phenyl propionate, phenyl butyrate, citrate, lactate, β-hydroxybutyrate, glycolate, malate, tartrate, methane sulfonate, propane sulfonate, naphthalene-1-sulfonate, naphthalene-2-sulfonate, or mandelate.

The acid addition salt of the present invention may be produced by a conventional method, for example, by dissolving the compound represented by chemical formula 1 in an excess of aqueous acid solution, and precipitating the salt using a water-miscible organic solvent, for example, methanol, ethanol, acetone, or acetonitrile.

Also, the compound represented by chemical formula 1 according to the present invention may be used in the form of a pharmaceutically acceptable metal salt by using a base. For example, an alkaline metal or alkaline earth metal salt may be obtained by dissolving the compound represented by chemical formula 1 in an excess of alkaline metal hydroxide or alkaline earth metal hydroxide solution, filtering off a non-dissolved compound salt, and evaporating and drying the filtrate. In this instance, as the metal salt, a sodium salt, a potassium salt, or a calcium salt is suitable in a pharmaceutical aspect. Also, a corresponding silver salt may be obtained by reacting an alkaline metal or alkaline earth metal salt with a suitable silver salt, for example, silver nitrate.

Meanwhile, the composition for preventing and treating influenza virus infection according to the present invention may be a pharmaceutical composition.

When the composition of the present invention is a pharmaceutical composition, the composition may include a pharmaceutically acceptable carrier. The composition including the pharmaceutically acceptable carrier may be variously formulated for oral or parenteral administration. For preparations, a diluent or an excipient such as a filler, a bulking agent, a binder, a wetting agent, a desintegrant, a surfactant, and the like may be generally added. A solid preparation for oral administration may be used as a tablet, a pellet, powder, a granule, a capsule, and the like, and may be obtained by mixing at least one compound with at least one excipient, for example, starch, calcium carbonate, sucrose or lactose, gelatine, and the like. Besides a basic excipient, a lubricant such as magnesium stearate or talc may be used. A liquid preparation for oral administration may be used as a suspension, a solution, an emulsion, a syrup, and the like, and may include a common diluent such as water or liquid paraffin, as well as a variety of excipients, for example, a wetting agent, a sweetener, a flavoring agent, a preservative, and the like. A preparation for parenteral administration may be used as a sterilized aqueous solution, a non-aqueous solvent, a suspension, an emulsion, a lyophilized preparation, a suppository, and the like. As a non-aqueous solvent or a suspending agent, propylene glycol, polyethylene glycol, plant oils such as olive oil, or injectable ester such as ethyl oleate may be used. As a suppository base, witepsol, macrogol, TWEEN® 61, cacao butter, laurinum, or glycerolgelatin may be used.

The pharmaceutical composition may be formulated as at least one selected from a tablet, a pellet, powder, a granule, a capsule, a suspension, a liquid, an emulsion, a syrup, a sterilized aqueous solution, a non-aqueous solvent, a lyophilized preparation, and a suppositorie.

The composition of the present invention may be administered in a pharmaceutically effective dosage. The term "pharmaceutical effective dosage" described herein refers to an amount sufficient to treat a disease at a reasonable benefit/danger ratio within the range applicable to a medical treatment, and an effective dosage level may be determined based on the type, disease severity, age, and gender of individual, type of infected virus, drug efficacy, sensitivity to medication, time and route of administration, ration of excretion, period of treatment, drug combination, and factors well known in the medical field.

However, for preferable effects, a dosage of the turmeric extract or its fraction according to the present invention may be 0.0001 to 100 mg/kg per day, preferably 0.001 to 100 mg/kg per day, and a dosage of the compound represented by chemical formula 1 may be 0.0001 to 100 mg/kg per day, preferably 0.001 to 10 mg/kg per day. The composition of the present invention may be administered alone or in combination with drugs, and may be administered sequentially or simultaneously with conventional drugs. Also, the composition may be administered in a single or multiple dose. Taking all the above factors into consideration, it is important to administer such a dosage as to obtain a maximum effect with a minimum amount without side effects, and the dosage may be easily determined by a person having an ordinary skill in the art.

The composition of the present invention may be used alone or in combination with operation, endocrinotherapy, drug treatment, and methods using a biological response modifier, to prevent and treat influenza virus infection.

Also, the present invention provides a use of a turmeric extract, turmeric fraction, or compound represented by the following chemical formula 1 in preventing and treating influenza virus infection, or a use of a turmeric extract, turmeric fraction, or compound represented by the following chemical formula 1 in preparing a drug for preventing and treating influenza virus infection:

[Chemical formula 1]

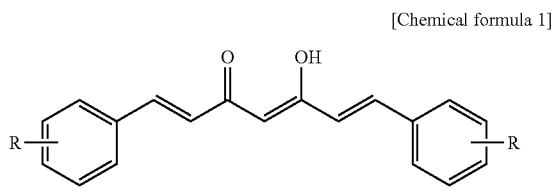

Also, the present invention provides a method for treating a disease caused by influenza virus infection including administering a pharmaceutically effective dosage of the composition for preventing and treating influenza virus infection to an individual infected or to be infected with influenza virus. The influenza virus may be influenza A virus, influenza B virus, or influenza C virus, preferably H1N1 influenza virus or H9N2 influenza virus. More preferably, the influenza virus may be rvH1N1 influenza A virus, H1N1 influenza virus (A/PR/8/34), or $H_9N_2$ influenza virus (A/Chicken/Korea/MS96/96). The disease caused by influenza virus infection may be influenza, cold, laryngopharyngitis, bronchitis, pneumonia, and particularly, bird flu, swine flu, or goat flu.

The term "individual" described herein refers to all animals including humans infected or to be infected with influenza virus, and the disease may be effectively prevented and treated by administering a composition including the extract, fraction, or compound of the present invention to the individual. For example, the composition of the present invention may treat humans infected with human influenza virus of a variety of influenza virus subtypes or variants.

Also, the composition of the present invention may treat humans infected with avian influenza virus of a variety of influenza virus subtypes or variants. Also, the composition of the present invention may treat chickens or swines infected with avian influenza virus of a variety of influenza virus subtypes or variants.

The composition of the present invention may be administered in combination with a conventional drug used for a disease caused by influenza virus infection. For example, the conventional drug may include, but is not limited to, Amatadine, Rimatadine, Zanamivir, and Oseltamivir.

The composition of the present invention may be administered via any general route as long as the composition can be delivered to a target tissue. The composition of the present invention may be administered by an intraperitoneal, intravenous, intramuscular, subcutaneous, intradermal, oral, intranasal, intralung, or rectal route of administration depending on the intent of administration, however the present invention is not limited in this regard. Also, the composition may be administered using any device capable of delivering an active ingredient to a target cell.

Further, the present invention provides a food composition comprising a turmeric extract, a turmeric fraction, or a compound represented by the following chemical formula 1 separated therefrom as an active ingredient to prevent and reduce influenza virus infection:

[Chemical formula 1]

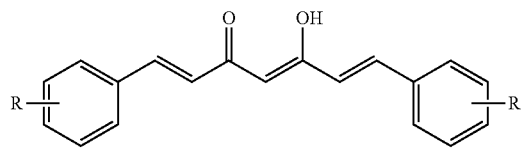

where R is independently hydrogen, a hydroxyl group, or $C_1$-$C_{10}$ alkoxy group.

In this instance, the compound represented by chemical formula 1 may be separated from the turmeric extract or turmeric fraction. More specifically, the compound represented by chemical formula 1 may be a compound represented by any one of the following chemical formulas 2 to 4.

[Chemical formula 2]

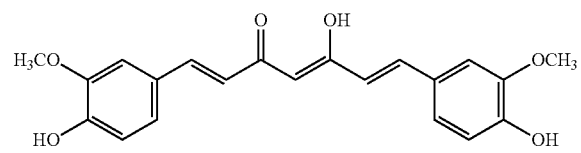

[Chemical formula 3]

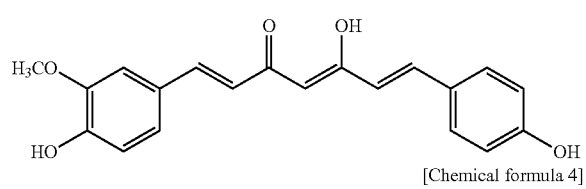

[Chemical formula 4]

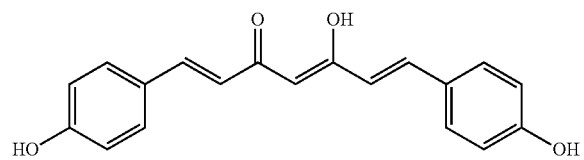

In other words, the turmeric extract, the turmeric fraction, or the compound represented by chemical formula 1 separated therefrom according to the present invention may be added to a food composition to prevent or reduce influenza virus infection.

According to the present invention, the food composition may be a functional food, and the "functional food" is a food with a body modulating function, and refers to a value added food that works on and is expressed at a specific target using physical, biochemical, and biotechnological methods. The ingredients of the functional food may be designed and processed to sufficiently exert a body control function involving biological defense, biorhythm control, and disease prevention and recovery on the body.

When the turmeric extract, the turmeric fraction, or the compound represented by chemical formula 1 separated therefrom according to the present invention is used as a food additive, the extract, fraction, or compound may be used as it is or may be used together with foods or food ingredients, and may be properly used by a conventional method. A mix ratio of active ingredients may be suitably determined depending on the purpose of use, for example, disease prevention or therapeutic treatment. Generally, when manufacturing foods or beverages, the turmeric extract, the turmeric fraction, or the compound represented by chemical formula 1 separated therefrom according to the present invention may be added in an amount of 0.01 to 10 w %, preferably 0.05 to 1 w %, based on the raw material composition. In the case of a long-term use for health, sanitation or diet, the amount may be less than the above range.

The food is not limited to a specific kind. For example, the food comprising the above substance may be meats, sausages, breads, chocolates, candies, snacks, cookies, pizza, ramen, noodles, gums, dairy products including ice creams, various soups, beverages, teas, health drinks, alcoholic beverages, vitamin complexes, and the like, and may include all traditional health foods.

The health beverage composition of the present invention may additionally contain a flavoring agent or natural carbohydrate, like a general beverage. The natural carbohydrate may be monosaccharide such as glucose and fructose, disaccharide such as maltose and sucrose, polysaccharide such as dextrin and cyclodextrin, or sugar alcohol such as xylitol, sorbitol and erythritol. The sweetener may be a natural sweetener such as thaumatin and a stevia extract, or a synthetic sweetener such as saccharin and aspartame. The content of the natural carbohydrate may be generally about 0.01 to 0.04 g, preferably about 0.02 to 0.03 g, per 100 d of the composition of the present invention.

In addition to the above, the composition of the present invention may contain a variety of additives, for example, nutrient, vitamin, electrolyte, a flavoring agent, a coloring agent, pectic acid and its salt, alginic acid and its salt, organic acid, a protective colloid thickening agent, a pH adjusting agent, a stabilizer, a preservative, glycerin, alcohol, a carbonating agent for carbonated beverages, and the like. The content of the additive is not particularly important, but may be generally selected within the range of 0.01 to 0.1 parts by weights per 100 parts by weight of the composition of the present invention. These additives may be used alone or in combination.

Further, the present invention provides a quasi-drug composition comprising a turmeric extract, a turmeric fraction, or a compound represented by the following chemical formula 1 separated therefrom as an active ingredient to prevent and reduce influenza virus infection:

[Chemical formula 1]

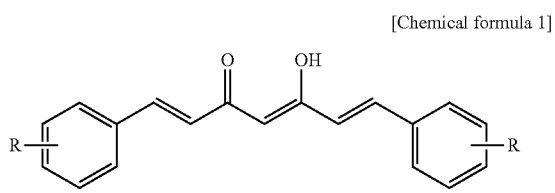

where R is independently hydrogen, a hydroxyl group, or $C_1$-$C_{10}$ alkoxy group.

In this instance, the compound represented by chemical formula 1 may be separated from the turmeric extract or turmeric fraction. More specifically, the compound represented by chemical formula 1 may be a compound represented by any one of the following chemical formulas 2 to 4.

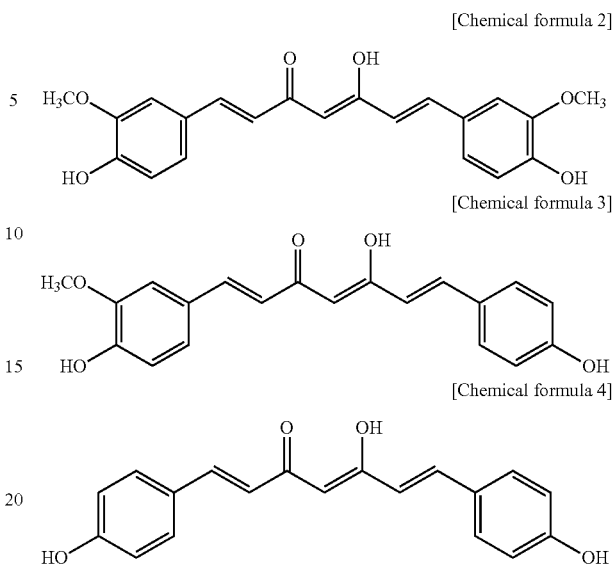

In other words, the composition of the present invention may be added to a quasi-drug composition to prevent or reduce influenza virus infection. When the turmeric extract, turmeric fraction, compound represented by chemical formula 1 separated therefrom according to the present invention is used as a quasi-drug additive, the turmeric extract, fraction, or compound may be used as it is or may be used together with quasi-drugs or quasi-drug ingredients, and may be properly used by a conventional method. A mix ratio of active ingredients may be suitably determined depending on the purpose of use, for example, disease prevention, health, or therapeutic treatment.

Preferably, the quasi-drug composition may be used in manufacturing a natural disinfectant, a feed additive, a disinfectant cleaner, a shower foam, a mouthwash, a wet tissue, a detergent soap, a hand-wash, a humidifier filler, a mask, an ointment, a filter filler, and the like.

Also, the present invention provides a composition comprising a turmeric extract, a turmeric fraction, or a compound represented by the following chemical formula 1 as an active ingredient to inhibit neuraminidase activity:

[Chemical formula 1]

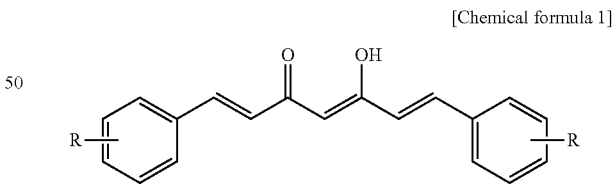

where R is independently hydrogen, a hydroxyl group, or $C_1$-$C_{10}$ alkoxy group.

In this instance, the neuraminidase may be derived from influenza A virus, influenza B virus, influenza C virus, *Clostridium perfringens*, or human, preferably H1N1 influenza virus or H9N2 influenza virus. More preferably, the influenza virus may be derived from rvH1N1 influenza A virus, H1N1 influenza virus (A/PR/8/34), or $H_9N_2$ influenza virus (A/Chicken/Korea/MS96/96).

Neuraminidase, also known as sialidase or acylneuraminyl hydrolase, is an enzyme present in animals and some microorganisms, and many microorganisms containing neuraminidase may cause diseases to humans and animals including poultry, horses, swines, seals, and the like. Accordingly, the composition for inhibiting neuraminidase activity according to the present invention may be useful in preventing and treating many diseases related to neuraminidase activity.

Also, the present invention provides a method for inhibiting neuraminidase activity including contacting the composition with a sample containing neuraminidase. In this instance, the contacting may be carried out by a conventional method, and the sample containing neuraminidase may be living organisms, tissues or cell cultivators, or biological samples such as blood, serum, urine, cerebrospinal fluid, tear, sputum, saliva, tissue, and the like, and may include neuraminidase-producing organisms, generally pathogenic organisms such as viruses. These samples may be put in any culture medium containing water, or an organic solvent/water mixture.

After the composition of the present invention is administered, the neuraminidase activity may be observed by any method including direct or indirect diagnosis of the neuraminidase activity. Also, quantitative, qualitative, or semi-quantitative diagnosis of neuraminidase activity, and observation of the physiological characteristics of living organisms may be used.

DETAILED DESCRIPTION

Hereinafter, the present invention will be described in detail through examples and experimental examples. However, the description proposed herein is just a preferable example for the purpose of illustrations only, not intended to limit the scope of the invention, so it should be understood that the examples are provided for a more definite explanation to an ordinary person skilled in the art.

Example 1

Preparation of Turmeric Extract

A turmeric used in this example is generally available in a medicinal herb shop or market. The steamed and dried radix of *Curcuma longa* Linne was purchased, and to effectively obtain an extract of the present invention, was milled in powder form. 1.6 kg of turmeric was dissolved in 7.5 l of 100% ethanol (EtOH), placed at room temperature for 5 days, and filtered through a filter paper, to obtain 170 g of a turmeric ethanol extract.

Example 2

Separation of Turmeric Fraction and Curcuminoid-Based Compound from Turmeric Extract and Purification 170 g of the turmeric ethanol extract obtained in example 1 was suspended in 1 l of water. A separatory funnel was placed, and the suspension was fractionally extracted with n-hexane and ethylacetate in sequence, to yield 23 g of an n-hexane soluble extract, 85 g of an ethylacetate soluble extract, and 34 g of a water soluble extract.

85 g of the obtained ethylacetate soluble extract was separated into 15 fractions Fr.-1 to Fr.-15 by silica gel column chromatography (500 g silica gel, mesh 70~230) using solvents of chloroform, methanol, and mixture thereof (80:1~1:1) as mobile phases. Among them, 16 g of the sixth fraction Fr.-6 was separated into 5 fractions Fr.-6-1 to Fr.-6-5 by silica gel column chromatography (30 g, mesh 230~400) using a mixed solvent of n-hexane and ethylacetate (20:1~1:1 (v/v)) as a mobile phase.

After performing silica gel column chromatography on Fr.-6-2 and Fr.-6-3 fractions (11 g) using solvents of chloroform, methanol, and mixture thereof (80:1~4:1) as mobile phases, a fraction obtained was developed by preparative TLC using a mixed solvent of n-hexane and ethylacetate (4:1 (v/v)) as a mobile phase, to yield 8 g of a pure compound 1. Also, 14 g of the eighth fraction Fr.-8 was repetitively separated by silica gel column chromatography (30 g, mesh 230~400) using a mixed solvent of n-hexane and ethylacetate (20:1~1:1 (v/v)) and a mixed solvent of chloroform and methanol (80:1~20:1 (v/v)) as mobile phases, to yield 0.4 g of a compound 2 and 0.2 g of a compound 3.

Example 3

Structural Analysis of Curcuminoid-Based Compound

The molecular weight and molecular formula of the curcuminoid-based compounds obtained in example 2 was determined using a VG high resolution GC/MS spectrometer (Election Ionization MS, Autospec-Ultima). Also, the molecular structure was determined through nuclear magnetic resonance analysis (Bruker AM500) using $^1$H-NMR, $^{13}$C-NMR, and 2D NMR spectroscopy materials.

Based on comparing the above results with those of published papers, curcumin, demethoxycurcumin and bis-demethoxycurcumin represented by chemical formulas 2 to 4 were identified (*Food Chem.* 265-272, 2009; *J. Nat. Prod.* 1227-1231, 2002; *J. Nat. Prod.* 1531-1534, 1998; *J. Agric. Food Chem.* 3668-3672, 2002). The analysis results are shown in detail below.

Compound 1: Curcumin

[Chemical formula 2]

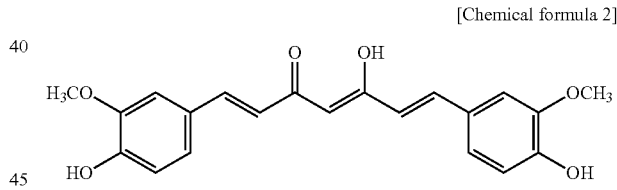

1) Property: light orange powder (m.p. 183° C.)
2) Molecular weight: 368.3
3) Molecular formula: $C_{21}H_{20}O_6$
4) $^1$H-NMR (acetone-$d_6$, 500 MHz) δ 7.62 (2H, d, J=15.80 Hz, H-4, H-4'), 7.35 (2H, d, J=1.91 Hz, H-6, H-6'), 6.83 (2H, H-3, H-5), 7.20 (2H, dd, J=8.3, 1.9 Hz, H-10, H-10'), 6.90 (2H, d, J=8.15 Hz, H-9, H-6'), 5.99 (1H, s, H-1), $^{13}$C-NMR (acetone-$d_6$, 125 MHz) δ 56.72, 102.01, 111.95, 116.64, 122.72, 124.25, 128.58, 141.81, 149.20, 150.44, 184.94.

Compound 2: Demethoxycurcumin

[Chemical formula 3]

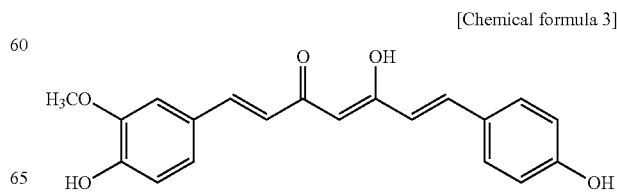

1) Property: orange powder (m.p. 220° C.)
2) Molecular weight: 338
3) Molecular formula: $C_{20}H_{18}O_5$
4) $^1$H-NMR (acetone-$d_6$, 500 MHz) δ 7.62-7.55 (4H), 7.34 (1H), 7.18 (1H), 6.89 (3H), 6.70 (2H), 5.97 (1H), $^{13}$C-NMR (acetone-$d_6$, 125 MHz) δ 56.38, 101.79, 111.53, 116.30, 116.89, 122.12, 122.35, 123.98, 127.77, 128.24, 131.06, 141.13, 141.48, 148.87, 150.13, 160.64, 184, 66.

Compound 3: Bisdemethoxycurcumin

[Chemical formula 4]

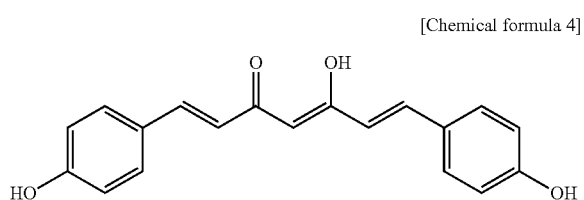

1) Property: orange powder (m.p. 224° C.).
2) Molecular weight: 308
3) Molecular formula: $C_{19}H_{16}O_4$
4) $^1$H-NMR (acetone-$d_6$, 500 MHz) δ 7.62-7.56 (6H), 6.91-6.87 (4H), 6.68-6.65 (2H), 5.98 (1H), $^{13}$C-NMR (acetone-$d_6$, 125 MHz) δ 101.82, 116.87, 122.11, 127.79, 131.06, 141.12, 160.58, 184, 62.

Example 4

HPLC Analysis of Turmeric Alcohol Extract and Fraction

The turmeric extract, the turmeric fraction, and the curcuminoid-based compounds obtained in examples 1 and 2 were analyzed by HPLC chromatography. In this example, Agilent 1200 series HPLC system with a pump and a variable wavelength detector (VWD) was used. In this instance, wavelength was 260 nm for optimum observation, and a flow rate of a solvent was 1.0 ml/min. In the sample preparation, an injection volume was 10 μl and a sample concentration was 10 mg/ml. In the HPLC analysis, ZORBAX-SB-18 column (5 μm, 150 mm×4.6 mm) was used. 20% acetonitrile (0 min), 25% acetonitrile (10 min), 35% acetonitrile (20 min), 50% acetonitrile (30 min), 60% acetonitrile (40 min), 70% acetonitrile (50 min), and 100% acetonitrile (60 min) were used as a mobile phase on the condition of polar distribution of water (containing 0.1% TFA) and acetonitrile (containing 0.1% TFA).

In this example, to measure the content of the curcuminoid-based compounds contained in each of the turmeric extract and the turmeric fraction, calibration curves were prepared under the same conditions as the above at 15.625, 31.25, 62.5, 125, 250, 500, and 1000 μg/ml of curcumin, demethoxycurcumin, and bisdemethoxycurcumin.

Based on the black line, the measurement results of the content of curcumin, demethoxycurcumin, and bisdemethoxycurcumin in each of the turmeric extract and the turmeric fraction showed that 106.0 g/kg of curcumin (extract), 45.4 g/kg of demethoxycurcumin (extract), and 64.6 g/kg of bisdemethoxycurcumin (extract) were contained in the turmeric ethanol extract, 114.3 g/kg of curcumin (fraction), 45.8 g/kg of demethoxycurcumin (fraction), and 66.4 g/kg of bisdemethoxycurcumin (fraction) were contained in the ethylacetate fraction, and 21.3 g/kg of curcumin (fraction), 7.3 g/kg of demethoxycurcumin (fraction), and 31.2 g/kg of bisdemethoxycurcumin (fraction) were contained in the hexane fraction.

The quantitative results are shown in Table 1 below.

TABLE 1

| Sample used | Content | | |
|---|---|---|---|
| | Curcumin | Demethoxycurcumin | Bisdemethoxycurcumin |
| Turmeric ethanol extract | 106.0 g/kg (Extract) | 45.4 g/kg(Extract) | 64.6 g/kg(Extract) |
| Turmeric ethylacetate fraction | 114.3 g/kg (Fraction) | 45.8 g/kg(Fraction) | 66.4 g/kg(Fraction) |
| Turmeric hexane fraction | 21.3 g/kg (Fraction) | 7.3 g/kg(Fraction) | 31.2 g/kg(Fraction) |

Further, by using the black line calculation, the measurement results of the content of curcumin, demethoxycurcumin, and bisdemethoxycurcumin in an alcohol extract of *Curcuma longa* Linne for area showed that 17.0 g/kg of curcumin (extract), 5.3 g/kg of demethoxycurcumin (extract), and 3.4 g/kg of bisdemethoxycurcumin (extract) were detected in a tuberous root, curcumin, demethoxycurcumin, and bisdemethoxycurcumin were not detected in a stem, and 2.8 g/kg of curcumin (fraction), 0.4 g/kg of demethoxycurcumin (fraction), and 6.8 g/kg of bisdemethoxycurcumin (fraction) were detected in a rhizome.

The quantitative results are shown in Table 2 below.

TABLE 2

| Sample used | Content (g/Kg, Content) | | |
|---|---|---|---|
| | Curcumin | Demethoxycurcumin | Bisdemethoxycurcumin |
| Ethanol extract of tuberous root | 17.0 | 6.3 | 3.4 |
| Ethanol extract of stem | — | — | — |
| Ethanol extract of rhizome | 2.8 | 0.4 | 6.8 |

Experimental Example 1

Determination of Neuraminidase A/Bervig_Mission/1/18 (rvH1N1) Inhibitory Activity of Turmeric Extract, Fraction, and Curcuminoid-Based Compound To determine the neuraminidase inhibitory activity of the turmeric extract, the turmeric fraction, and the curcuminoid-based compounds separated therefrom that were obtained in examples 1 and 2 of the present invention, neuraminidase (R&D SYSTEM, 4858-NM) of a recombinant rvH1N1 influenza A virus of 1918 Spanish flu virus (A/Bervig_Mission/1/18) was used. 2'-(4-trimethylumbelliferyl)-α-D-N-acetyl-neuraminic acid sodium salt from Sigma was used as a substrate.

The turmeric extract and its fraction of examples 1 and 2 were dissolved in methanol. As a substrate, 2'-(4-trimethylumbelliferyl)-α-D-N-acetyl-neuraminic acid sodium salt (final concentration 200 μM) was added to 20 μL of each solution. The result was mixed with 80 μL of a tris buffer (pH 7.5) containing 5 mM $CaCl_2$ and 200 mM NaCl, and reacted with 50 μL of neuraminidase (final enzyme concentration 0.05 ng/μL) as a zymogen at 25° C. for 10 minutes. The neuraminidase inhibitory activity was determined by measuring the light absorption at 365 nm and the light emission at 445 nm using a fluorescence spectroscope.

The measurement results are shown in Table 3 below.

TABLE 3

| Substance | Neuraminidase inhibitory activity $(IC_{50})$[1] A/Bervig-Mission/ 1/18 (rvH1N1) |
|---|---|
| Turmeric ethanol extract | 3.1 μg/mL |
| Turmeric hexane fraction | 262.0 μg/mL |
| Turmeric ethylacetate fraction | 0.9 μg/mL |
| Turmeric water fraction | 61.5 μg/mL |
| Curcumin | 3.0 μM |
| Demethoxycurcumin | 3.0 μM |
| Bisdemethoxycurcumin | 6.0 μM |

[Note]
[1] a result value is an average of two tests.

As shown in Table 3, the determination results of neuraminidase inhibitory activity of each of the turmeric extract, fraction, and curcuminoid-based compounds according to the present invention showed that the turmeric ethanol extract had an $IC_{50}$ value of 3.1 μg/mL against influenza virus neuraminidase, the turmeric hexane fraction had an $IC_{50}$ value of 262.0 μg/mL, the turmeric ethylacetate fraction had an $IC_{50}$ value of 0.9 μg/mL, the turmeric water fraction had an $IC_{50}$ value of 61.5 μg/mL, curcumin and demethoxycurcumin had each an $IC_{50}$ value of 3.0 μM, and bisdemethoxycurcumin had an $IC_{50}$ value of 6.0 μM. Accordingly, it was determined through the above results that the turmeric extract, its fraction, and curcuminoid-based compounds according to the present invention had excellent neuraminidase inhibitory activity.

Experimental Example 2

Determination of Influenza Virus Inhibitory Activity of Curcuminoid-Based Compound Separated from Turmeric Extract, Ethylacetate Fraction, and Ethanol Extract To determine the antiviral effects of the curcuminoid-based compounds, ethylacetate fraction, and ethanol extract separated from the turmeric extract on influenza virus H1N1 (A/PR/8/34) and $H_9N_2$ (A/Chicken/Korea/MS96/96), a test below was carried out in vitro using a Madin-Darby canine kidney (MDCK, ATCC CCL-34) cell of a dog.

First, MDCK cells were put in a 96-well microplate at a density of $1\times10^5$/well, and incubated in a culture medium (EMEM) containing 100 units penicillin, 100 μg streptomycin and 10% FBS. When the MDCK cells are grown as a monolayer, the MDCK cells were washed twice with a culture medium (EMEM) only containing antibiotic. Each of H1N1 and H9N2 strains was diluted with 100 $TCID_{50}$, and put in an EP tube. The curcuminoid-based compounds, ethylacetate fraction and ethanol extract separated from the turmeric extract diluted with dimethylsulfoxide (DMSO) were put in each tube based on concentration, followed by reaction at 4° C. for 1 hour. After the lapse of 1 hour, the reacted solutions were inoculated into 3 wells of the pre-washed MDCK cells at each concentration, followed by incubation at 35° C. for 1 hour (hereinafter referred to as a test sample). Under the same conditions, non-infected+non-administered cells (MDCK cells not infected with an H1N1 or H9N2 strain and not administered with the curcuminoid-based compound) and infected+non-administered cells (MDCK cells infected with an H1N1 or H9N2 strain and not administered with curcumin), incubated at 35° C. for 1 hour, were each set as a control and a virus control. After the lapse of 1 hour, the culture mediums of the plate were all removed, and the cells were washed once with PBS. 10 μg/mL of a culture medium (EMEM) containing antibiotic and 10 μg/mL trypsin was dispensed in each well of the cells, followed by incubation at 35° C. for 48 to 72 hours. The incubation was performed for 48 to 72 hours until the infected+non-administered cells (virus control) have cytopathic effects (CPE). The state of the cells was observed with an inverted microscope every day. After the cells were incubated for 48 to 72 hours, 10 ml of a cell counting kit-8 (Dojin, Kumanoto, Japan, tetrazolium salt WST-8) was added to each well to determine the cell survival, followed by reaction at 35° C. for 2 hours, and the absorbance was measured at 450 nm. In this instance, the antiviral effects (inhibition (%)) of the curcuminoid-based compounds, ethylacetate fraction, and ethanol extract separated from the turmeric extract of the present invention were calculated using the following mathematical formula 1 in comparison with the non-infected+non-administered cells (control) and the infected+non-administered cells (virus control). The results are shown in Table 4 below.

Mathematical formula 1

$$\text{Inhibition}(\%) = \frac{OD \text{ value of test sample} - OD \text{ value of infected} + \text{non-administered control}}{OD \text{ value of non-infected} + \text{non-administered control} - OD \text{ value of infected} + \text{non-administered control}} \times 100$$

where the OD value is absorbance measured at 450 nm.

Meanwhile, to determine the cell degeneration inhibitory effects of the curcuminoid-based compounds, ethylacetate fraction, and ethanol extract separated from the turmeric extract on influenza virus H1N1 (A/PR/8/34) and H9N2 (A/Chicken/Korea/MS96/96), MDCK cells were washed twice with a culture medium (EMEM) only containing antibiotic, inoculated with influenza virus (H1N1 or H9N2 strain), and incubated at 35° C. for 1 hour. After the lapse of 1 hour, the virus solution used in inoculation was completely removed, and the curcuminoid-based compounds, ethylacetate fraction, and ethanol extract separated from the turmeric extract were each inserted into the virus-inoculated MDCK cells. Subsequently, the cell degeneration inhibitory effects (inhibition (%)) of the curcuminoid-based compounds, ethylacetate fraction, and ethanol extract separated from the turmeric extract of the present invention were determined using the above mathematical formula 1. The results are shown in Table 4 below.

TABLE 4

| | Antiviral effect | | | | | |
|---|---|---|---|---|---|---|
| | H1N1(A/PR/8/34) | | | H9N2(A/Chicken/Korea/MS96/96) | | |
| Substance | $CC_{50}(\mu M)^a$ | $EC_{50}(\mu M)^b$ | $SI^c$ | $CC_{50}(\mu M)^a$ | $EC_{50}(\mu M)^b$ | $SI^c$ |
| Tamiflu | >200 | 18.5 | >10.8 | >200 | <1 | >200 |
| Curcumin | 94.1 | 7.1 | 13.3 | 94.1 | 18.6 | 5.1 |
| Demethoxycurcumin | 97.0 | 8.0 | 23.1 | 97.0 | 18.2 | 5.3 |
| Bisdemethoxycurcumin | >200 | 28.1 | >7.1 | >200 | >200 | <1 |
| Ethylacetate fraction | 82.1 µg/mL | 9.0 µg/mL | 9.1 | 82.1 µg/mL | 20.0 µg/mL | 4.1 |
| Ethanol extract | 55.7 µg/mL | 8.7 µg/mL | 6.4 | 55.7 µg/mL | 30.4 µg/mL | 1.8 |
| | Cell degeneration inhibitory effect | | | | | |
| | H1N1(A/PR/8/34) | | | H9N2(A/Chicken/Korea/MS96/96) | | |
| Substance | $CC_{50}(\mu M)^a$ | $EC_{50}(\mu M)^b$ | $SI^c$ | $CC_{50}(\mu M)^a$ | $EC_{50}(\mu M)^b$ | $SI^c$ |
| Tamiflu | >200 | 3.0 | >66.7 | >200 | <1 | >200 |
| Curcumin | 94.1 | 40.7 | 2.3 | 94.1 | 10.9 | 8.6 |
| Demethoxycurcumin | 97.0 | 60.8 | 1.6 | 97.0 | 24.9 | 3.9 |
| Bisdemethoxycurcumin | >200 | 141.5 | >1.4 | >200 | 181.6 | >1.1 |
| Ethylacetate fraction | 82.1 µg/mL | 23.5 µg/mL | 3.5 | 82.1 µg/mL | 11.6 µg/mL | 7.1 |
| Ethanol extract | 55.7 µg/mL | 27.8 µg/mL | 2.0 | 55.7 µg/mL | 31.5 µg/mL | 1.8 |

[Note]
$^a CC_{50}$, 50% cytotoxic concentration
$^b EC_{50}$, 50% antiviral concentration
$^c SI$, selective index, $CC_{50}/EC_{50}$ a. The curcuminoid-based compounds, ethylacetate fraction and ethanol extract were each mixed with virus, followed by reaction at 4° C. for 1 hour, and MDCK cells were infected with the virus. After the lapse of 1 hour, the cells were washed once with PBS and a culture medium (EMEM) containing 10 mg/mL trypsin was dispensed. The cells were incubated at 35° C. for 48 to 72 hours.

b. After 1 hour of the virus infection, the medium including the virus was removed and replaced with a fresh medium containing each of the curcuminoid-based compounds, ethylacetate fraction, and ethanol extract, and then the cells were incubated for 48 to 72 hours.

c. $CC_{50}/EC_{50}$ as selective index (SI)

As shown in Table 4, the curcuminoid-based compounds had excellent antiviral effects on an H1N1 strain exhibiting a selective index (SI) of 13.3, 23.1, and greater than 7.1. Also, the curcuminoid-based compounds exhibited a selective index (SI) of 5.1, 5.3, and less than 1.0 against an H9N2 strain. Accordingly, it was determined that the curcuminoid-based compounds had antiviral effects on a variety of virus strains. The turmeric ethylacetate fraction and turmeric ethanol extract had excellent antiviral effects on an H1N1 strain, exhibiting a selective index (SI) of 9.1 and 6.4, respectively. According to the observation results of the cell morphology with an inverted microscope, it was found that MDCK cells inoculated with virus (H1N1 or H9N2) were almost degenerated, leading to 90 to 100% of cytopathic effects, while virus-infected MDCK cells treated with the curcuminoid-based compounds, ethylacetate fraction, and ethanol extract exhibited a similar aspect to a non-infected+non-administered control.

Furthermore, the curcuminoid-based compounds had cell degeneration inhibitory effects on H1N1 and H9N2. In particular, the curcuminoid-based compounds had excellent cell degeneration inhibitory effects on an H9N2 strain exhibiting a selective index (SI) of 8.6, 3.9, and greater than 1.1, and had cell degeneration inhibitory effects on an H1N1 strain exhibiting a selective index (SI) of 2.3, 1.6, and greater than 1.4. According to the observation results of the cell morphology with an inverted microscope, it was found that MDCK cells inoculated with virus (H1N1 or H9N2) were almost degenerated, leading to 90 to 100% of cytopathic effects, while virus-infected MDCK cells treated with the curcuminoid-based compounds, ethylacetate fraction, and ethanol extract exhibited a similar aspect to a non-infected+non-administered control.

Accordingly, the composition of the present invention may be useful in preventing and treating influenza virus infection because the composition has antiviral effects by directly working on the virus before the virus infects cells, and has excellent cell degeneration inhibitory effects by preventing the virus from releasing from cells through replication after the cells are infected with the virus.

Experimental Example 3

Acute Toxicity Test of Compound of the Present Invention

To determine the acute toxicity of the compounds of the present invention, a test below was performed.

Specific pathogens free (SPF) C57BL/6J mice including 12 female and 12 male, aged 6 weeks (sample), were grouped into four groups (3 female mice and 3 male mice as a test group), and bred in an animal room under temperature of 22±3° C., humidity of 55±10%, and illumination of 12L/12D. Before the test, the mice were gone through domestication for 1 week. The mice were allowed to freely eat laboratory animal feeds (feed for mice and rats, CJ Corporation in Seoul, Republic of Korea) and sterile water.

A sample was prepared by adding 0.5% of TWEEN®80 to each of the compounds represented by chemical formulas 2 to 4 obtained in example 2 at a concentration of 50 mg/mL, and administered in a dosage of 0.04 mL (100 mg/kg), 0.2 mL (500 mg/kg), and 0.4 mL (1,000 mg/kg) per 20 g of mouse weight. The sample was orally administered in a single dose, and after administration, side effect or survival was observed for 7 days. That is, on the day of administration, the general symptomatic change and survival were observed after 1 hour, 4 hours, 8 hours, and 12 hours of administration, and from the next day of administration to the seventh day, were observed once or more each in the forenoon and afternoon every day.

The acute toxicity test results showed that all the mice administered with the sample did not have a noteworthy clinical sign and there was no dead mouse. Also, the toxicity change was not observed in the weight change, blood test, biochemical examination of blood, and autopsy findings.

The compounds of the present invention did not show the toxicity change in all the mice until a dosage is 1,000 mg/kg, and accordingly, it was identified that the compounds of the present invention are a stable substance having 1,000 mg/kg or more of an oral $LD_{50}$, that is, a minimum lethal dose.

Hereinafter, manufacturing examples of a pharmaceutical preparation and a health food comprising a turmeric extract, a turmeric fraction, a curcuminoid-based compound separated therefrom, or its pharmaceutically acceptable salt are described.

Manufacturing Example 1

Manufacture of Pharmaceutical Preparation 1-1. Powder
2 g of a turmeric extract, fraction, compound separated therefrom, or its salt
1 g of lactose
These ingredients were mixed and packed in an air-tight container to manufacture a pharmaceutical preparation in powder form.

1-2. Tablet
100 mg of a turmeric extract, fraction, compound separated therefrom, or its salt
100 mg of corn starch
100 mg of lactose
2 mg of magnesium stearate
These ingredients were mixed and compressed by a conventional tablet manufacturing method to manufacture a pharmaceutical preparation in tablet form.

1-3. Capsule
100 mg of a turmeric extract, fraction, compound separated therefrom, or its salt
100 mg of corn starch
100 mg of lactose
2 mg of magnesium stearate
These ingredients were mixed and enclosed in a gelatin capsule by a conventional capsule manufacturing method to manufacture a pharmaceutical preparation in capsule form.

1-4. Injection
10 µg/ml of a turmeric extract, fraction, compound separated therefrom, or its salt
Dilute hydrochloric acid BP to adjust pH to 3.5
Maximum 1 ml of sodium chloride injection BP
A turmeric extract, fraction, compound separated therefrom, or its salt was dissolved in a proper volume of sodium chloride injection BP. Dilute hydrochloric acid BP for adjusting the pH to 3.5 and sodium chloride injection BP for adjusting the volume were sufficiently mixed with the resulting solution. 5 ml type I clear glass ampoule was filled with the solution, sealed by fusing the glass under an upper grid of air, and sterilized by autoclaving at 120° C. for 15 minutes or more, to manufacture a pharmaceutical preparation in injection form.

Manufacturing Example 2

Manufacture of Health Food 2-1. Cooking Condiment
0.2 to 10 w % of a turmeric extract, fraction, compound separated therefrom, or its salt was used in manufacturing cooking condiments for health promotion.

2-2. Tomato Ketchup and Sauce
0.2 to 1.0 w % of a turmeric extract, fraction, compound separated therefrom, or its salt was added to tomato ketchups or sauces to manufacture tomato ketchups or sauces for health promotion.

2-3. Flour Food
0.1 to 5.0 w % of a turmeric extract, fraction, compound separated therefrom or its salt was mixed with flour, and the mixture was used in making breads, cakes, cookies, crackers, and noodles, to manufacture foods for health promotion.

2-4. Soup and Gravy
0.1 to 1.0 w % of a turmeric extract, fraction, compound separated therefrom or its salt was added to soups and gravies to manufacture processed meat products, soups for noodles, and gravies for health promotion.

2-5. Ground Beef
10 w % of a turmeric extract, fraction, compound separated therefrom or its salt was added to ground beef to manufacture ground beef for health promotion.

2-6. Dairy Product
0.1 to 1.0 w % of a turmeric extract, fraction, compound separated therefrom or its salt was added to milk, and the milk was used in manufacturing various dairy foods including butter and ice-cream.

2-7. Cereal Powder
Unpolished rice, barley, glutinous rice, and adlay were pregelatinized by a known method, dried, roasted, and milled into powder having a particle size of 60 mesh using a mill.

Black soybean, black sesame, and *perilla* were steamed by a known method, dried, roasted, and milled into powder having a particle size of 60 mesh using a mill.

A turmeric extract, fraction, compound separated therefrom or its salt was evaporated under reduced pressure using a vacuum evaporator, sprayed, hot-air dried, and milled into dried powder having a particle size of 60 mesh using a mill.

The obtained cereals, seeds, and dried powder of the turmeric extract, fraction, compound separated therefrom or its salt were mixed at the following ratio.

75 w % of cereals including 35 w % of unpolished rice, 15 w % of adlay, and 25 w % of barley
23 w % of seeds including 7 w % of perilla, 9 w % of black soybean, and 7 w % of black sesame
1 w % of turmeric extract, fraction, compound separated therefrom or its salt
0.5 w % of lingzhi mushroom
0.5 w % of rehmanni 2-8. Carbonated Beverage
5 to 10 w % of sugar, 0.05 to 0.3 w % of citric acid, 0.005 to 0.02 w % of caramel, and 0.01 to 1 w % of vitamin C were mixed. Purified water was added to make the total composition 100 w %, yielding a syrup. The syrup was sterilized at 85 to 98° C. for 20 to 180 seconds, and mixed with a coolant at a ratio by volume of 1:4, to prepare a beverage composition. 0.5 to 0.82 volume % of carbonic acid gas was injected into the beverage composition to manufacture carbonated beverages comprising a turmeric extract, fraction, compound separated therefrom or its salt.

2-9. Health Beverage 1 w % of a turmeric extract, fraction, compound separated therefrom or its salt was uniformly mixed with an additive including 0.5 w % of high fructose corn syrup, 2 w % of oligosaccharide, 2 w % of sugar, 0.5 w % of common salt, and 94 w % of water, then flash-pasteurized, and packed in a small packing container such as a vial, a PET bottle, and the like, to manufacture health beverages.

2-10. Vegetable Juice 0.5 g of a turmeric extract, fraction, compound separated therefrom or its salt was added to 1,000 ml of tomato or carrot juices to manufacture vegetable juices for health promotion.

2-11. Fruit Juice 0.1 g of a turmeric extract, fraction, compound separated therefrom or its salt was added to 1,000 ml of apple or grape juices to manufacture fruit juices for health promotion.

What is claimed is:

1. A method for treating an influenza virus infection in a human or animal in need thereof the method comprising administering to said human or animal therapeutically effective amounts of a composition consisting essentially of a hexane or ethyl acetate turmeric extract.

2. The method according to claim 1, wherein the extract contains any of the following chemical formulas 2 to 4:

Chemical formula 2

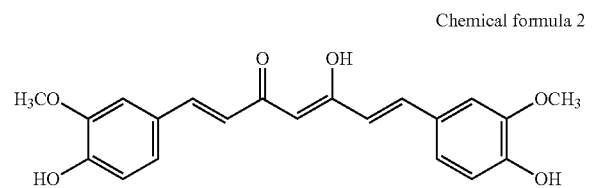 [SMILES: COc1cc(/C=C/C(=O)/C=C(O)/C=C/c2ccc(O)c(OC)c2)ccc1O]

Chemical formula 3

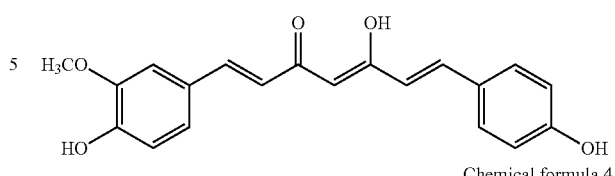

Chemical formula 4

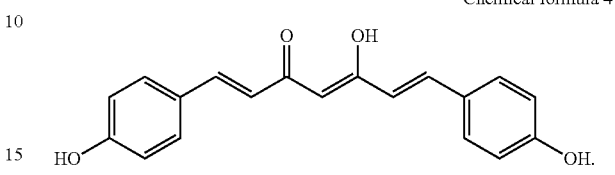

3. The method according to claim 1, wherein the turmeric is *Curcuma wenyujin* (Y. H. Chen et C. Ling), *Curcuma longa* Linne, *Curcuma longa* Salisb., *Curcuma zedoaria, Curcuma kwansiensis* (S. G. Lee et C. F. Liang), *Curcuma aeruginosa, Curcuma phaeocaulis* Val. (Zingiberaceae), or *Curcuma domestica*.

4. The method according to claim 1, wherein the turmeric is a tuberous root.

5. The method according to claim 1, wherein the influenza virus is influenza A virus, influenza B virus, or influenza C virus.

6. The method according to claim 1, wherein the influenza virus is H1N1 influenza virus or H9N2 influenza virus.

7. The method according to claim 1, wherein the influenza virus is rvH1N1 influenza A virus, H1N1 influenza virus A/PR/8/34, or H9N2 influenza virus A/Chicken/Korea/MS96/96.

8. The method according to claim 1, wherein the influenza is bird flu, swine flu, or goat flu.

9. The method of claim 1, wherein the human or animal also has a cold, bronchitis, pneumonia or laryngopharyngitis.

* * * * *